United States Patent
Viegas et al.

(10) Patent No.: US 6,497,157 B1
(45) Date of Patent: Dec. 24, 2002

(54) INTRINSIC DISSOLUTION APPARATUS WITH STATIONARY SAMPLE HOLDER

(75) Inventors: Tacey X. Viegas, Birmingham, AL (US); Gerald Brinker, North Brunswick, NJ (US); Michael Cai, Old Bridge, NJ (US)

(73) Assignee: Distek, Inc., North Brunswick, NJ (US)

( * ) Notice: Subject to any disclaimer, the term of this patent is extended or adjusted under 35 U.S.C. 154(b) by 140 days.

(21) Appl. No.: 09/711,287

(22) Filed: Nov. 13, 2000

Related U.S. Application Data
(60) Provisional application No. 60/167,744, filed on Nov. 29, 1999.

(51) Int. Cl.[7] .......................... G01N 33/15; G01N 33/00; G01N 13/00
(52) U.S. Cl. ............................................. 73/866; 73/863
(58) Field of Search ...................... 73/866, 863, 864.91; 436/174, 177

(56) References Cited

U.S. PATENT DOCUMENTS

| | | | |
|---|---|---|---|
| 3,169,888 A | * 2/1965 | Ryan et al. ..................... 127/30 |
| 3,344,076 A | * 9/1967 | Wilcox, Jr. ................... 510/439 |
| 3,557,003 A | * 1/1971 | Morris et al. ................ 510/298 |
| 3,791,221 A | 2/1974 | Kirschner et al. ............. 73/866 |
| 3,791,222 A | 2/1974 | Goodhart et al. ............. 73/866 |
| 4,223,008 A | * 9/1980 | Gregory ..................... 424/480 |
| 4,593,563 A | 6/1986 | Laine et al. ................ 73/865.8 |
| 5,004,614 A | * 4/1991 | Staniforth ................... 424/466 |
| 5,360,615 A | * 11/1994 | Yu et al. ...................... 424/455 |
| 5,486,364 A | * 1/1996 | King et al. .................. 424/488 |
| 5,589,649 A | 12/1996 | Brinker et al. ................. 73/866 |
| 6,030,643 A | * 2/2000 | Adams et al. ............... 424/464 |
| 6,245,917 B1 | * 6/2001 | Bosch et al. ............. 548/321.1 |

FOREIGN PATENT DOCUMENTS

WO     WO 97/20028     6/1997          C11D/17/00

OTHER PUBLICATIONS

U.S. Pharmacopeia, Section 711, pp. 1941–1943, Jan. 1, 2000.
Supplement 1 to the U.S. Pharmacopeia 24 and the National Formulary 19, Nov. 1, 1999, pp. 2706–2707, "Section 1087 on Intrinsic Dissolution".

(List continued on next page.)

*Primary Examiner*—Thomas P. Noland
(74) *Attorney, Agent, or Firm*—Steve Mendelsohn

(57) ABSTRACT

For intrinsic dissolution testing, a drug pellet (i.e., the dissolution test sample) is retained within a cylindrical recess in a sample holder that is placed at the bottom of a dissolution vessel containing an appropriate dissolution medium with the sample holder oriented with the drug pellet facing up. During the testing cycle, the dissolution medium may be stirred, e.g., using a conventional USP 2 rotating paddle, while the sample holder (and drug pellet) remain stationary at the bottom of the vessel. The orientation of the drug pellet during testing (i.e., facing up) decreases the likelihood of retention of air bubbles formed at the surface of the drug pellet (which bubbles could otherwise decrease the effective dissolution rate), thereby providing more accurate and consistent intrinsic dissolution test results.

8 Claims, 3 Drawing Sheets

OTHER PUBLICATIONS

"Solid–State Chemistry of Drugs," by Stephen R. Byrn, Ralph R. Pfeiffer, and Joseph G. Stowell, Chapter 6, pp. 91–101, Published by SSCI, Inc. (West Lafayette, IN), 2nd Edition, 1999.

"Automated Potentiometric Procedure for Studying Dissolution Kinetics of Acidic Drugs under Sink Conditions," by Fred L. Underwood and Donald E. Cadwallader, Journal of Pharmaceutical Sciences, vol. 67, No. 8, Aug. 1978, pp. 1163–1167.

"Improved Holder for Intrinsic Dissolution Rate Studies," by John H. Wood, John E. Syarto, and Herbert Letterman, J. Pharm. Sci. 54, pp. 1068 (1965).

"Dissolution Bioavailability & Bioequivalence," by Hamed M. Abdou, PhD, pp. 26–27, Published by Mack Publishing Co. (Easton, PA), 1989.

Website page "http://vankel.com/accessor.htm," Mar. 12, 1998, 1 page.

Brochure from Vankel Industries, Inc., 2 pages, May 1996.

* cited by examiner

INTRINSIC DISSOLUTION APPARATUS WITH STATIONARY SAMPLE HOLDER

CROSS-REFERENCE TO RELATED APPLICATIONS

This application claims the benefit of the filing date of U.S. provisional application No. 60/167,744, filed on Nov. 29, 1999.

BACKGROUND OF THE INVENTION

1. Field of the Invention

The present invention relates to the field of dissolution testing and, in particular, to apparatuses for intrinsic dissolution testing of pharmaceuticals in solid, semi-solid, and transdermal dosage form.

2. Description of the Related Art

In general, dissolution testing is used to determine the rate of dissolution of a material in a solvent or solution. For example, dissolution testing may be used to determine the rate of dissolution of pharmaceuticals in dosage form in specific dissolution mediums to simulate digestion in a human. The requirements for such dissolution testing apparatuses are provided in United States Pharmacopeia (USP), Edition XXII, Section 711, Dissolution (1990).

Conventional dissolution testing apparatuses have one or more dissolution vessels in which dissolution media may be placed. One conventional configuration of a dissolution testing apparatus has, for each dissolution vessel, a paddle-type stirring element consisting of a metal shaft with a metal blade at the end. After placing the dosage to be dissolved loose at the bottom of the vessel, the stirring element is lowered into the dissolution medium near the center of the vessel and rotated at a specified rate (typically measured in revolutions per minute (rpm)) for a specified duration. Samples of the dissolution media may be periodically withdrawn from the vessels to determine the degree of dissolution of the dosages as a function of time.

One of the problems with this conventional configuration for dissolution testing is that the total exposed surface area of the test sample changes (i.e., decreases) over the testing cycle as the dosage is dissolved. Since the instantaneous dissolution rate is a function of the current total exposed surface area of the test sample, it is hard to correlate how dissolution rate varies as a function of time when the surface area also changes over the testing cycle. To address this problem, intrinsic dissolution testing may be performed.

The intrinsic dissolution rate is defined as the rate of dissolution of a pure pharmaceutical active when conditions such as the total exposed surface area of the sample as well as the temperature, agitation-stirring speed, pH, and ionic strength of the dissolution medium are kept constant. The determination of the intrinsic dissolution rate allows for screening of drug candidates and in understanding their solution behavior under different bio-physiological conditions.

The implementation of "sameness" analysis has been presented and applied in a number of scientific guidelines for demonstrating formulation equivalencies among semi-solids, immediate-release solid oral, and extended-release solid oral dosage forms. Conventional test methods for these analyses involve the use of vertical diffusion cells, enhancer cells, and the USP apparatuses 1 and 2. The evaluation of the intrinsic dissolution of active pharmaceutical ingredients (API) is a means to demonstrate chemical equivalency. The need to demonstrate "sameness" among APIs has risen due to changes in the bulk active synthesis, the final crystallization steps, particle size and surface area, polymorphism and scale-up issues regarding batch-size and manufacturing site.

Currently the USP lists the Wood's Intrinsic Dissolution Apparatus from VanKel Industries, Inc., of Cary, N.C. as the official apparatus for determination of intrinsic dissolution rates. See USP 24-NF 19 Supplement 1, Section 1087, Intrinsic Dissolution (Released Nov. 1, 1999).

FIG. 1 shows a cross-sectional view of a prior-art intrinsic dissolution test configuration 100 based on the Wood's Intrinsic Dissolution Apparatus. Test configuration 100 comprises a rotatable shaft 102 positioned over the center of a round-bottomed dissolution vessel 104. At the end of shaft 102 is a die 106 rigidly connected to shaft 102 by a die holder 108. A drug pellet (i.e., the test sample) is formed and retained within a cylindrical recess 110 centered on the bottom face 112 of die 106. After an appropriate dissolution medium (not shown) is placed within vessel 104, shaft 102 is lowered into the dissolution medium within vessel 104 to position the bottom of die 106 at a specified distance (e.g., 1 to 1.5 inches) above the bottom of the vessel. During intrinsic dissolution testing, shaft 102 is rotated, thereby rotating the drug pellet contained within recess 110. Dissolution is achieved by shear-like motion of the pellet within the dissolution medium. Since the drug pellet has the same shape as cylindrical recess 110, in theory, the total exposed surface area of the test sample should remain substantially constant during the dissolution testing cycle as the drug pellet dissolves.

FIG. 2 shows an exploded, cross-sectional view of conventional equipment used to form the drug pellet within cylindrical recess 110 of die 106 of FIG. 1. As shown in FIG. 2, die 106 is secured to a base plate 202 by a number of screw pins inserted through openings 204 in base plate 202 and screwed into corresponding tapped holes 206 on the bottom face 112 of die 106. Test sample material 207 in powder form is then placed within a cylindrical die cavity 208 within die 106, and pressure is applied with a plunger 210 to press the powdered material against base plate 202 to form a cylindrical drug pellet at the bottom of cavity 208. Retaining male end 212 of plunger 210 within cavity 208 forms cylindrical recess 110 of FIG. 1. Die holder 108 is then screwed onto threaded end 214 of die 106 with an intervening O ring or other gasket 216 that prevents the dissolution medium from reaching the drug pellet through the upper end of cavity 208. Base plate 202 may then be removed (by removing the screw pins) to provide the subassembly of die holder 108 and die 106 shown in FIG. 1 with a drug pellet formed and positioned within recess 110 of die 106, ready for intrinsic dissolution testing.

One of the problems with the conventional intrinsic dissolution test configuration of FIG. 1 relates to the formation of air bubbles at the exposed (i.e., bottom) surface of the test sample. Such air bubbles can interfere with dissolution testing by decreasing the effective dissolution rate. Air bubbles may come from different sources. First of all, air bubbles may be formed when the test sample is initially lowered from air into the dissolution medium. In addition, air bubbles may be formed as the test sample dissolves either from air trapped within the drug pellet or as a by-product of the dissolving of the sample material itself.

Another problem is that the shaft and die assembly of FIG. 1 may wobble when operated at high rotation speeds (e.g., 100 rpm). Such wobbling may alter the effective dissolution rate, thereby leading to further inaccuracies in the test results.

In addition, the temperature of the dissolution medium may change (e.g., drop about 2° C.) when the relatively massive shaft and die assembly are first inserted into the dissolution medium, with heat being removed from the dissolution medium through the shaft.

SUMMARY OF THE INVENTION

The present invention is directed to a configuration for intrinsic dissolution testing that addresses these problems with the prior art. According to the present invention, a drug pellet is retained within a sample holder that is positioned at the bottom of the dissolution vessel with the drug pellet facing up. The dissolution medium may then be stirred, e.g., using a conventional rotating paddle positioned above the stationary sample holder.

Intrinsic dissolution testing equipment according to the present invention decreases the likelihood of air bubbles adversely affecting test results during the testing cycle. Moreover, since the sample holder is stationary during the testing cycle, any wobbling of the rotating paddle at high speeds will not directly affect the effective dissolution rate. In addition, since the sample holder is placed at the bottom of the vessel before dissolution testing begins, there is no significant temperature change to the dissolution medium when the relatively low-mass rotating paddle is lowered into the dissolution medium. Each of these factors may contribute to an improved ability of the present invention to achieve more accurate and consistent intrinsic dissolution test results.

In one embodiment, the present invention is a method for performing intrinsic dissolution testing, comprising the steps of (a) forming a test sample within a recess of a sample holder; (b) placing the sample holder within a dissolution vessel containing a dissolution medium with the sample holder oriented with the test sample facing up; and (c) performing intrinsic dissolution testing for the test sample with the sample holder substantially stationary within the dissolution vessel.

In another embodiment, the present invention is an apparatus for intrinsic dissolution testing, comprising (a) a die having a die cavity; (b) a plunger configured to be inserted within the die cavity to define a recess for retaining a test sample at a first side of the die; and (c) a cap configured to be secured over a second side of the die to form a sample holder, wherein the cap has a shape that conforms sufficiently to the shape of the bottom of a vessel used during the intrinsic dissolution testing to keep the sample holder substantially stationary at the bottom of the vessel with the test sample retained within the recess oriented facing up within a dissolution medium.

BRIEF DESCRIPTION OF THE DRAWINGS

Other aspects, features, and advantages of the present invention will become more fully apparent from the following detailed description, the appended claims, and the accompanying drawings in which:

DETAILED DESCRIPTION

Figure 3:
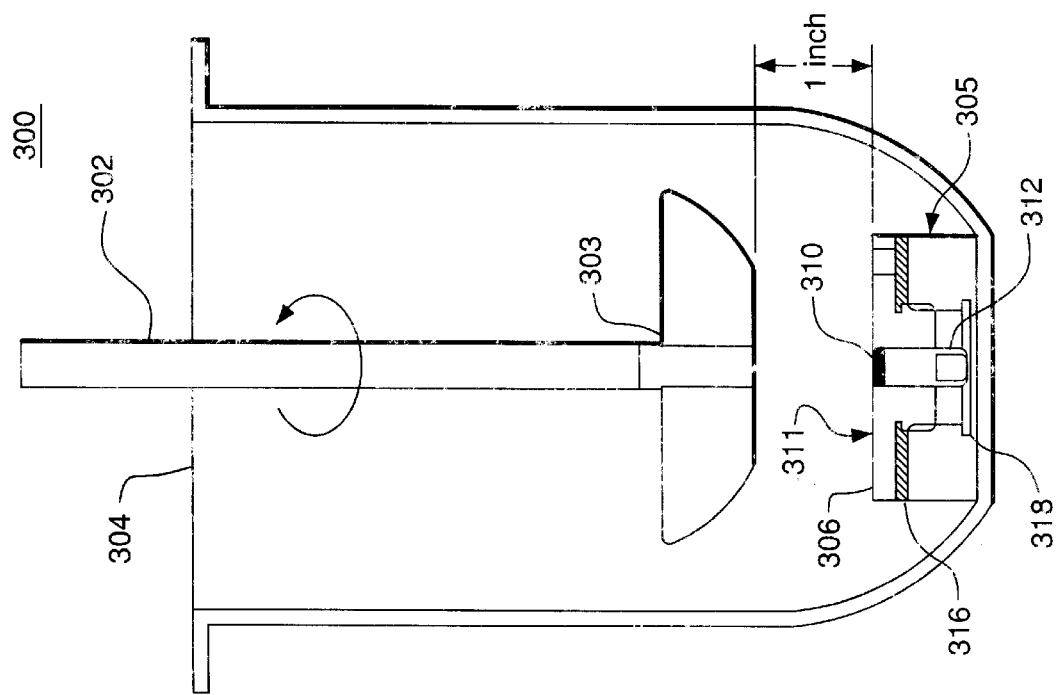
FIG. 3 shows a cross-sectional view of an intrinsic dissolution test configuration, according to one embodiment of the present invention.

FIG. 3 shows a cross-sectional view of an intrinsic dissolution test configuration 300, according to one embodiment of the present invention. Test configuration 300 comprises a rotatable shaft 302 having an attached paddle 303 positioned over the center of a flat-bottomed dissolution vessel 304. In a preferred implementation, paddle 303 is a conventional USP apparatus 2 paddle typically used in non-intrinsic dissolution testing. Resting at the center of the bottom of vessel 304 is a sample holder 305 configured to hold a drug pellet (i.e., the test sample) within a cylindrical recess 310 at the center of top surface 311 of sample holder 305.

As shown in FIG. 3, sample holder 305 comprises a die 306 having a central cylindrical (e.g., 0.8-cm diameter/0.5-$cm^2$ area) cavity within which a cylindrical plunger 312 is placed to form recess 310. A plastic cap 318 is secured over the bottom of plunger 312 and die 306 with an intervening gasket 316 to form a "water-tight" seal that prevents liquid from reaching the drug pellet from the lower end of the central cylindrical die cavity. For intrinsic dissolution testing, sample holder 305 is placed within vessel 304 with the drug pellet in recess 310 oriented facing up.

Figure 4:
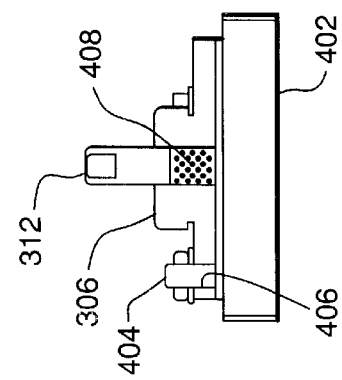
FIG. 4 shows a cross-sectional view of equipment used to form the drug pellet within the cylindrical recess of the die of FIG. 3.

FIG. 4 shows a cross-sectional view of equipment used to form the drug pellet within cylindrical recess 310 of die 306 of FIG. 3. As shown in FIG. 4, die 306 is secured to a base plate 402 by nuts and washers that are screwed over a number of threaded pins 404 (i.e., in this embodiment, three pins) that extend through corresponding openings 406 in die 306. Test sample material in powder form is then placed within central cylindrical die cavity 408 within die 306, and pressure is applied by plunger 312 (e.g., using a bench-top Carver hydraulic press (not shown) for 4–5 minutes at 2000 PSI) to press the powdered material against base plate 402 to form a drug pellet at the bottom of cavity 408. Retaining plunger 312 within cavity 408 forms cylindrical recess 310 in sample holder 305 of FIG. 3.

Figure 5:
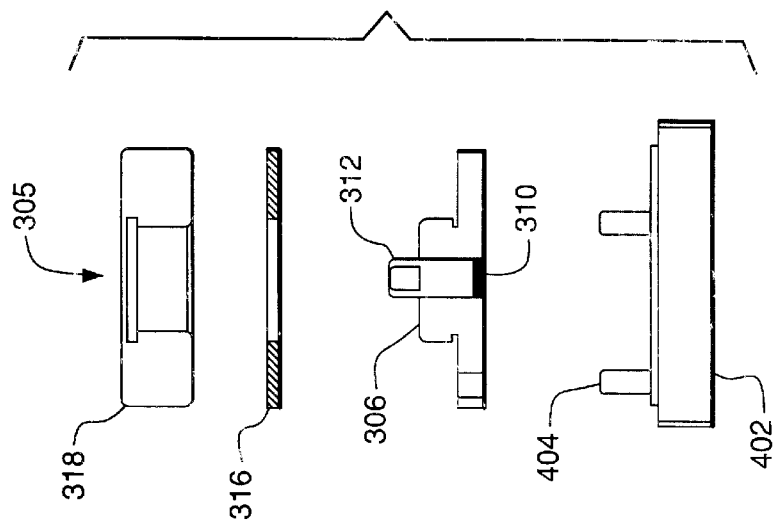
FIG. 5 shows an exploded, cross-sectional view of the sample holder of FIG. 3.

FIG. 5 shows an exploded, cross-sectional view of sample holder 305 of FIG. 3. As indicated in FIG. 5, after the subassembly of die 306 and plunger 312 with the drug pellet retained within recess 310 is removed from base plate 402 (by removing the nuts and washers from pins 404), plastic cap 318 is then secured onto plunger 312 with intervening gasket 316, for example, by screwing tapped cap 318 over the threaded top portion of die 306.

Referring again to FIG. 3, after securing gasket 316 and plastic cap 318 onto the die/plunger subassembly, sample holder 305 of FIG. 5 is turned over and placed (e.g., using a pair of forceps) at the center of the bottom of dissolution vessel 304 containing an appropriate dissolution medium (not shown) to position the drug pellet for dissolution testing. In a preferred implementation, the dimensions of the flat portion at the bottom of dissolution vessel 304 (e.g., a 5.38-cm diameter circle) correspond to the dimensions of plastic cap 318 to permit sample holder 305 to settle in a perfectly horizontal position, and without shifting during the stirring of the dissolution medium. Rotatable shaft 302 can then be lowered into the dissolution medium to position paddle 303 at a specified distance (e.g., 1 inch) from the top surface 311 of sample holder 305 and to rotate at a specified rated (e.g., 50 rpm), such that sample holder 305 remains stationary at the bottom of vessel 304 during the testing cycle.

At appropriate time intervals, an automated sample collector (not shown) removes aliquots from the dissolution medium for analysis. The data from the analysis would be used to provide pertinent intrinsic dissolution properties of the test compound. The time interval for sampling can vary, for example, from 2 to 30 minutes, depending on the properties of the drug and the dissolution medium used. Suitable dissolution equipment for these operations includes a Distek Model 2100B or 5100 Dissolution System and a Distek Model 2230A Autosampler, all from Distek, Inc. of North Brunswick, N.J.

Figure 8:
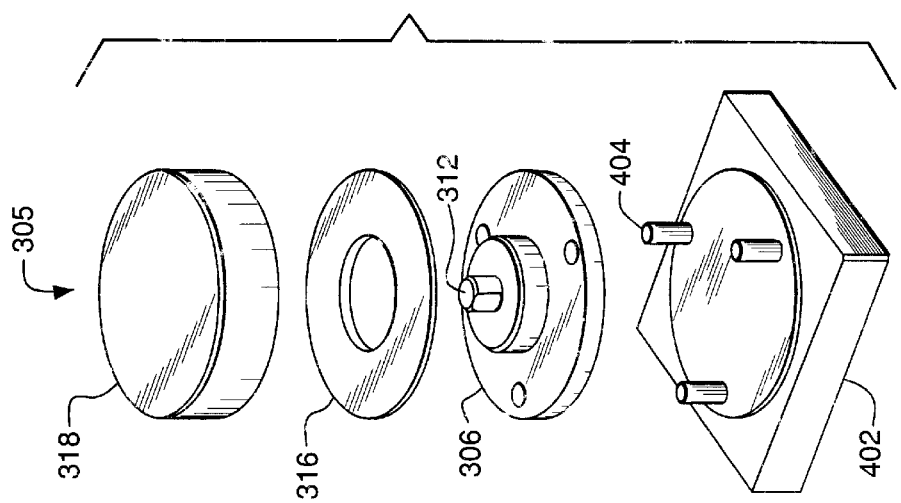
FIGS. 6–8 show isometric views of intrinsic dissolution test equipment corresponding to the cross-sectional views of FIGS. 3–5, respectively.
Figure 7:
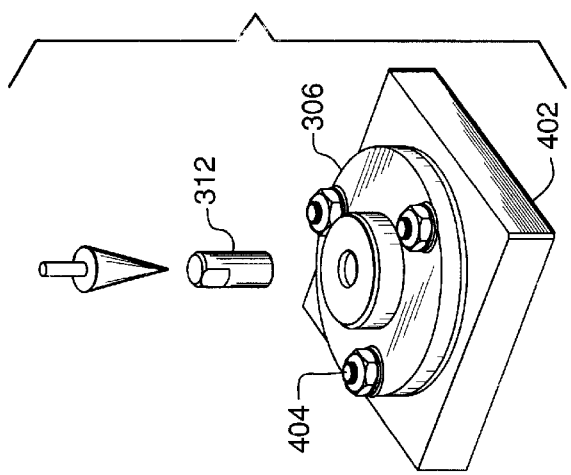
Figure 6:
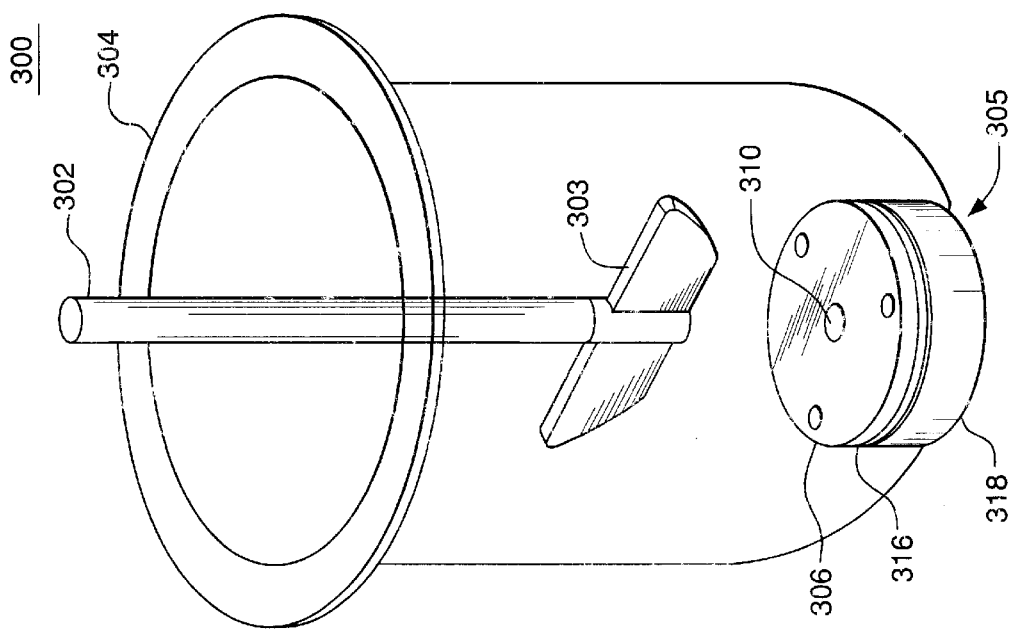

FIGS. 6–8 show isometric views of intrinsic dissolution test equipment corresponding to the cross-sectional views of FIGS. 3–5, respectively. Note that, prior to insertion of sample holder 305 into the dissolution medium, it may be desirable to plug up or otherwise cover the (three) recesses in sample holder 305 corresponding to openings 406 in die 306 to avoid additional disturbance to the flow of the dissolution medium during the testing cycle.

Figure 1:
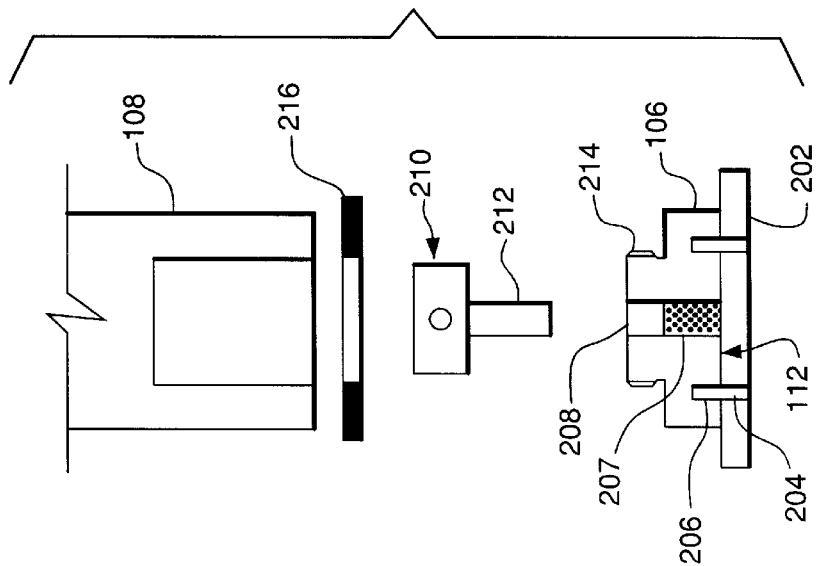
FIG. 1 shows a cross-sectional view of a prior-art intrinsic dissolution test configuration based on the Wood's Intrinsic Dissolution Apparatus.

Because the drug pellet is oriented within the dissolution medium with its exposed surface facing up (as opposed to the prior art configuration of FIG. 1 in which the drug pellet is oriented facing down), the likelihood that air bubbles will remain (e.g., trapped) at the exposed surface of the test sample is decreased with the present invention. If air bubbles are formed during the dissolution testing cycle, then the motion of the dissolution medium over the surface of the drug pellet in combination with gravitational effects will likely carry the air bubbles up and away from the surface. Since the likelihood of artificial and random decreases in effective dissolution rates due to air bubbles is decreased relative to the prior art configuration of FIG. 1, the intrinsic dissolution test configuration of the present invention may be able to provide more accurate and consistent dissolution test results.

Moreover, since the present invention can be used with conventional USP apparatus 2 paddles, such as paddle 303 of FIG. 3, intrinsic dissolution testing can be performed using the same basic configuration as that used for conventional (i.e., non-intrinsic) USP 2 dissolution testing, with the addition of sample holder 305 and the use of a flat-bottomed dissolution vessel.

In a preferred implementation of the present invention, die 306 is made from 316 stainless steel, plunger 312 is made from hardened steel, base plate 402 is made of polished hardened steel, plastic cap 318 is made of polypropylene, and gasket 316 is preferably either a Viton™ or Neoprene™ gasket. Die 306 preferably has a weight of 144 g, a height of 1.27 cm, and a diameter of 5.38 cm. Plastic cap 318 also preferably has a diameter of 5.38 cm to match the preferred diameter of the flat portion at the bottom of dissolution vessel 304.

Figure 2:
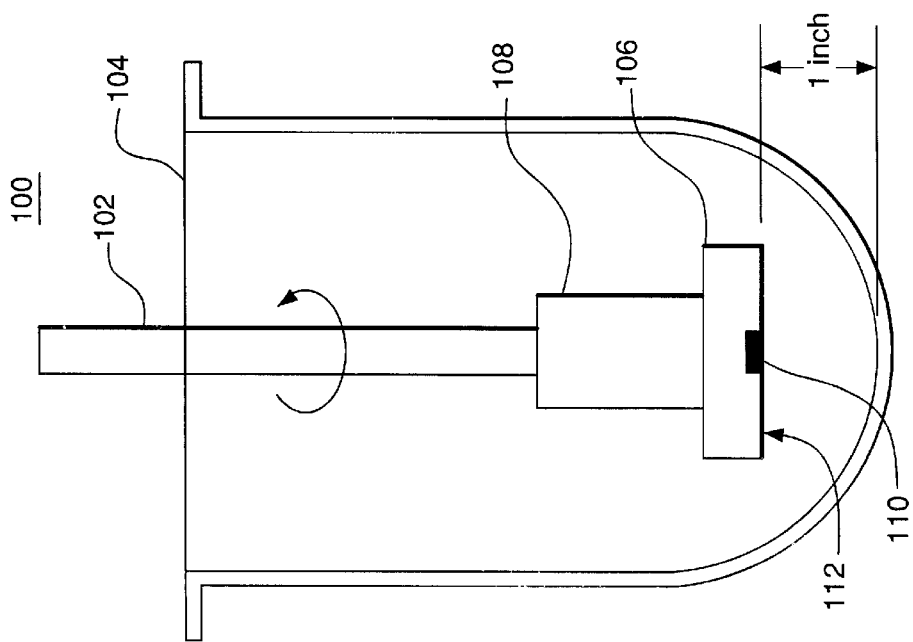
FIG. 2 shows an exploded, cross-sectional view of conventional equipment used to form the drug pellet within the cylindrical recess of the die of FIG. 1.

Although the present invention has been described in the context of a sample holder that is placed at the bottom of a flat-bottomed dissolution vessel, in general, the shape of the bottom of the sample holder (e.g., as dictated by the shape of the plastic cap used to seal the die/plunger subassembly) needs to conform sufficiently with the shape of the bottom of the dissolution vessel in order to keep the sample holder stationary at the center of the bottom of the dissolution vessel during the testing cycle. For example, a round-bottomed dissolution vessel, such as vessel 104 of FIG. 2, could in theory be used with a sample holder having a plastic cap with a rounded shape that corresponds with the shape of the bottom of the vessel, although the flat configuration is preferred.

In addition, although the present invention has been described in the context of a sample holder in which the plunger is retained within the die during dissolution testing, those skilled in the art will understand that, depending on the characteristics of the test sample material, the present invention may be able to be implemented using a procedure in which the plunger is removed from the die cavity after forming the drug pellet, but before sealing the die with the cap and gasket. It may also be possible to perform dissolution testing without using a separate gasket if the cap alone provides sufficient sealing of the die cavity.

Furthermore, although the present invention has been described in the context of intrinsic dissolution testing in which the dissolution medium is stirred, those skilled in the art will understand that the present invention can also be applied to intrinsic dissolution testing in which the dissolution medium is not stirred.

Moreover, although the present invention has been described in the context of intrinsic dissolution testing in which the test sample is a cylindrical drug pellet having a circular cross-section, formed within a cylindrical die cavity, those skilled in the art will understand that the present invention can also be applied to intrinsic dissolution testing in which the test sample has a non-cylindrical shape, such as a rectilinear pellet having a rectangular (e.g., square) cross-section, formed within a rectilinear die cavity. In addition, the present invention is not limited to intrinsic dissolution testing of drugs and other pharmaceuticals. The present invention can be applied to the testing of drug-powder blends in order to study and differentiate dissolution profiles of pellets that have been compressed with pressures between 500 and 3000 PSI. In general, the present invention can be applied to perform intrinsic dissolution testing on any soluble material in any appropriate dissolution medium. Typical test samples include solid chemical compounds having a crystalline morphology and semi-solid creams, ointments, and pastes.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. An apparatus for intrinsic dissolution testing, comprising:
   (a) a die having a die cavity;
   (b) a plunger configured to be inserted within the die cavity to define a recess for retaining a test sample at a first side of the die; and
   (c) a cap configured to be secured over a second side of the die to form a sample holder,
   wherein the cap has a shape that conforms sufficiently to the shape of the bottom of a vessel used during the intrinsic dissolution testing to keep the sample holder substantially stationary at the bottom of the vessel with the test sample retained within the recess oriented facing up within a dissolution medium, wherein the die has a plurality of openings corresponding to a plurality of threaded mounting pins of a base plate, such that the die is configured to be secured onto the base plate for formation of the test sample by pressing powdered test material within the die cavity against the base plate using the plunger.

2. The apparatus of claim 1, wherein the cap is configured to be secured over the die with an intervening gasket.

3. The apparatus of claim 1, wherein the cap is a tapped plastic cap that is configured to be screwed onto a threaded portion of the die.

4. The apparatus of claim 1, wherein the shape of the bottom of the vessel and the corresponding shape of the cap are flat circles.

5. The apparatus of claim 1, further comprising a rotatable paddle configured to stir the dissolution medium during the intrinsic dissolution testing.

6. The apparatus of claim 5, wherein the rotatable paddle is a USP apparatus 2 paddle.

7. The apparatus of claim 1, wherein:

the cap is a tapped plastic cap that is configured to be screwed onto a threaded portion of the die with an intervening gasket; and the shape of the bottom of the vessel and the corresponding shape of the cap are flat circles.

8. The apparatus of claim 7, further comprising a rotatable paddle configured to stir the dissolution medium during the intrinsic dissolution testing, wherein the rotatable paddle is a USP apparatus 2 paddle.

* * * * *